United States Patent
Komoto et al.

(10) Patent No.: US 8,334,379 B2
(45) Date of Patent: Dec. 18, 2012

(54) PROCESS FOR PRODUCING IMIDAZO[1,2-B]PYRIDAZINE COMPOUND

(75) Inventors: Ichiro Komoto, Nishinomiya (JP); Kazuaki Sasaki, Ibaraki (JP); Tomohiko Gotou, Oita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 659 days.

(21) Appl. No.: 12/064,832

(22) PCT Filed: Aug. 22, 2006

(86) PCT No.: PCT/JP2006/316790
§ 371 (c)(1),
(2), (4) Date: May 5, 2010

(87) PCT Pub. No.: WO2007/026621
PCT Pub. Date: Mar. 8, 2007

(65) Prior Publication Data
US 2010/0234597 A1    Sep. 16, 2010

(30) Foreign Application Priority Data
Aug. 30, 2005    (JP) .................. 2005-248845

(51) Int. Cl.
C07D 487/00    (2006.01)
(52) U.S. Cl. .................. 544/236; 544/235
(58) Field of Classification Search .......... 544/235, 544/236
See application file for complete search history.

(56) References Cited

U.S. PATENT DOCUMENTS

| 5,017,212 A | 5/1991 | Ishida et al. |
| 2005/0032650 A1 | 2/2005 | Tanaka et al. |
| 2009/0312333 A1* | 12/2009 | Kenda et al. ............ 514/248 |

FOREIGN PATENT DOCUMENTS

| JP | 1-316379 A | 12/1989 |
| JP | 01316379 A | * 12/1989 |
| JP | 10-338692 A | 12/1998 |
| JP | 2004123690 A | 4/2004 |

OTHER PUBLICATIONS

V. Laba et al., 25 Khimiko-Farmatsevticheskii Zhurnal, 27-29 (1991).*
J.H. H Poupaert, Drug Design: Basic Principles and Applications, in 2 Encyclopedia of Pharmaceutical Technology 1362-1369, 1367 (James Swarbrick ed., 3rd ed., 2007).*
N.G. Anderson, Practical Process & Research Development 81-111 (2000).*
Caplus Accession No. 115:29070 (CAS, Entered STN Jul. 27, 1991).*

* cited by examiner

*Primary Examiner* — James O Wilson
*Assistant Examiner* — Alexander R Pagano
(74) *Attorney, Agent, or Firm* — Panitch Schwarze Belisario & Nadel LLP

(57) ABSTRACT

A process for producing an imidazo[1,2-b]pyridazine compound represented by the formula (2):

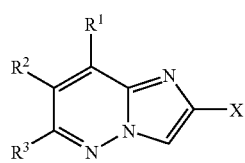

(2)

wherein $R^1$, $R^2$ and $R^3$ are the same or different and each represents a hydrogen atom, a halogen atom, an alkyl group which may be substituted with a halogen atom or atoms, an alkenyl group which may be substituted with a halogen atom or atoms, or an alkoxy group which may be substituted with a halogen atom or atoms, which comprises reacting a 2,3-dihydropyridazine compound represented by the formula (1):

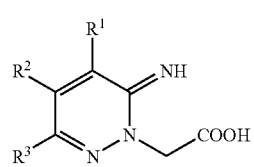

(1)

wherein $R^1$, $R^2$ and $R^3$ are the same meanings as defined above, with a phosphorus oxyhalide in the presence of an organic base which is in an amount of 0.5 mole or more relative to 1 mole of the 2,3-dihydropyridazine compound and 1 mole or less relative to 1 mole of the phosphorus oxyhalide.

5 Claims, No Drawings

PROCESS FOR PRODUCING IMIDAZO[1,2-B]PYRIDAZINE COMPOUND

CROSS-REFERENCE TO RELATED APPLICATION

This application is a section 371 of International Application No. PCT/JP2006/316790, filed Aug. 22, 2006, which was published in the Japanese language on Mar. 8, 2007 under International Publication No. WO 2007/026621 A1 and the disclosure of which is incorporated herein by reference.

TECHNICAL FIELD

The present invention relates to a process for producing an imidazo[1,2-b]pyridazine compound.

BACKGROUND ART

An imidazo[1,2-b]pyridazine compound is useful as an intermediate of pharmaceuticals and pesticides. For example, 2,6-dichloroimidazo[1,2-b]pyridazine is an important compound as an intermediate of sulfonylurea herbicides (e.g. U.S. Pat. No. 5,017,212 and U.S. Pat. No. 4,994,571). As processes for producing 2,6-dichloroimidazo[1,2-b]pyridazine, a process comprising reacting 3-imino-6-chloro-2,3-dihydropyridazine-2-acetic acid with phosphorus oxychloride has been known (e.g. JP patent No. 2863857).

DISCLOSURE OF THE INVENTION

The present invention provides a process for producing an imidazo[1,2-b]pyridazine compound represented by the formula (2):

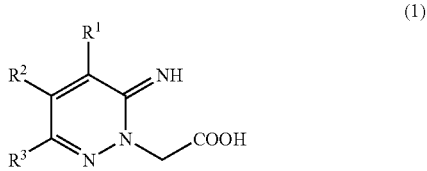

wherein $R^1$, $R^2$ and $R^3$ are the same or different and each represents a hydrogen atom, a halogen atom, an alkyl group which may be substituted with a halogen atom or atoms, an alkenyl group which may be substituted with a halogen atom or atoms, or an alkoxy group which may be substituted with a halogen atom or atoms, and X represents a halogen atom. The process comprises reacting a 2,3-dihydropyridazine compound represented by the formula (1):

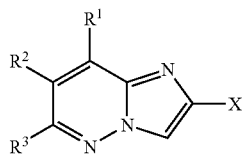

wherein $R^1$, $R^2$ and $R^3$ are the same meanings as defined above, with a phosphorus oxyhalide in the presence of an organic base which is in an amount of 0.5 mole or more relative to 1 mole of the 2,3-dihydropyridazine compound represented by the formula (1) and 1 mole or less relative to 1 mole of the phosphorus oxyhalide.

BEST MODE FOR CARRYING OUT THE PRESENT INVENTION

In the formula of a 2,3-dihydropyridazine compound represented by the formula (1):

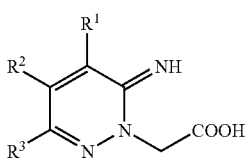

(hereinafter, simply referred to as the 2,3-dihydropyridazine compound (1)), $R^1$, $R^2$ and $R^3$ are the same or different and each represents a hydrogen atom, a halogen atom, an alkyl group which may be substituted with a halogen atom or atoms, an alkenyl group which may be substituted with a halogen atom or atoms, or an alkoxy group which may be substituted with a halogen atom or atoms.

Examples of the halogen atom include a fluorine, chlorine and bromine atom.

Examples of the alkyl group which may be substituted with a halogen atom or atoms include a C1-C6 linear, branched chain or cyclic unsubstituted alkyl group such a methyl, ethyl, propyl, isopropyl, butyl, isobutyl, sec-butyl, tert-butyl, pentyl, hexyl, cyclopentyl and cyclohexyl group; and those wherein at least one hydrogen atom of the above-mentioned unsubstituted alkyl groups is substituted with the above-mentioned halogen atom such as a fluoromethyl, chloromethyl, bromomethyl, trifluoromethyl, 1-chloroethyl, 1-bromoethyl, 1,1,1-trifluoroethyl, 1-chloropropyl, 1-bromopropyl and 1,1,1-trifluoropropyl group.

Examples of the alkenyl group which may be substituted with a halogen atom or atoms include a C2-C6 linear, branched chain or cyclic unsubstituted alkenyl group such as an ethenyl, 1-propenyl, 2-propenyl, 2-methyl-1-propenyl, 1,2-propadienyl, 1-butenyl, 2-butenyl, 1,3-butadienyl, 1-pentenyl, 1-hexenyl and 1-cyclohexenyl group; and those wherein at least one hydrogen atom of the above-mentioned unsubstituted alkenyl groups is substituted with the above-mentioned halogen atom such as a 2-chloro-1-propenyl, 2,2-dichloroethenyl, 2-chloro-2-fluoroethenyl and 3-bromo-1-methyl-1-propenyl group.

Examples of the alkoxy group which may be substituted with a halogen atom or atoms include a C1-C6 linear or branched chain or cyclic unsubstituted alkoxy group such a methoxy, ethoxy, propoxy, isopropoxy, butoxy, sec-butoxy, tert-butoxy, pentyloxy, hexyloxy, cyclopropyloxy, cyclopentyloxy and cyclohexyloxy group; and those wherein at least one hydrogen atom of the above-mentioned unsubstituted alkoxy groups is substituted with the above-mentioned halogen atom such as a fluoromethoxy, chloromethoxy, bromomethoxy, trifluoromethoxy, 1-chloroethoxy, 1-bromoethoxy, 1,1,1-trifluoroethoxy, 1-chloropropoxy, 1-bromopropoxy and 1,1,1-trifluoropropoxy group.

Examples of the 2,3-dihydropyridazine compound (1) include 3-imino-2,3-dihydropyridazine-2-acetic acid, 3-imino-6-chloro-2,3-dihydropyridazine-2-acetic acid, 3-imino-6-methyl-2,3-dihydropyridazine-2-acetic acid, 3-imino-6-methoxy-2,3-dihydropyridazine-2-acetic acid, 3-imino-6-ethoxy-2,3-dihydropyridazine-2-acetic acid, 3-imino-6-trifluoromethyl-2,3-dihydropyridazine-2-acetic acid, 3-imino-4-methyl-2,3-dihydropyridazine-2-acetic acid and 3-imino-4,6-dimethyl-2,3-dihydropyridazine-2-acetic acid.

As the 2,3-dihydropyridazine compound (1), a commercially available one may be used and one produced according to the method described in JP patent No. 2863857 or the like may be used.

Examples of the phosphorus oxyhalide include phosphorus oxychloride and phosphorus oxybromide. As the phosphorus oxyhalide, a commercially available one is usually used. The amount thereof to be used may be 1 mole or more relative to 1 mole of the 2,3-dihydropyridazine compound (1). There is no specific upper limit and it is preferably 1 to 10 moles and more preferably 1.5 to 6 moles relative to 1 mole of the 2,3-dihydropyridazine compound (1).

Examples of the organic base include a tertiary amine such as trimethylamine, triethylamine, diisopropylethylamine and N,N-dimethylaniline; and a nitrogen-containing heterocyclic compound such as 2-methyl-5-ethylpyridine and pyridine. The organic amine may be in a form of free or in a form of salt of hydrohalogenic acid such as hydrochloric acid and hydrobromic acid. As the organic base, a commercially available one is usually used. When the hydrohalogenic acid salt of the organic base is used, a commercially available one may be used and one prepared from the organic base and the hydrogen halide may be used. When the hydrohalogenic acid salt of the organic base is used, it is preferred that the halogen atom of the hydrohalogenic acid is same as the halogen atom of the phosphorus oxyhalide.

The amount of the organic base is 0.5 mole or more relative to 1 mole of 2,3-dihydropyridazine compound (1) and 1 mole or less relative to 1 mole of the phosphorus oxyhalide.

The reaction of 2,3-dihydropyridazine compound (1) and the phosphorus oxyhalide may be conducted in the absence of a solvent and in the presence of an inert solvent. Examples of the inert solvent include an aromatic hydrocarbon solvent such as toluene, xylene and mesitylene; an aliphatic hydrocarbon solvent such as decane; a halogenated aromatic hydrocarbon solvent such as monochlorobenzene; and a halogenated aliphatic hydrocarbon solvent such as tetrachloroethane. The amount thereof to be used is not particularly limited.

The reaction temperature is usually 60 to 180° C. and preferably 80 to 130° C.

The reaction of 2,3-dihydropyridazine compound (1) and the phosphorus oxyhalide is usually conducted by mixing 2,3-dihydropyridazine compound (1), the phosphrous oxyhalide and the organic base followed by adjusting at the predetermined temperature. The mixing order is not particularly limited, and a method comprising mixing 2,3-dihydropyridazine compound (1) with the phosphorus oxyhalide followed by mixing the mixture obtained with the organic base and a method comprising mixing 2,3-dihydropyridazine compound (1) with the organic base followed by mixing the mixture obtained with and the phosphorus oxyhalide are preferable. In the viewpoint of inhibiting the side reaction, 2,3-dihydropyridazine compound (1), the phosphorus oxyhalide and the organic base are preferably mixed at less than 60° C., and more preferably at 0 to 40° C.

The present reaction may be conducted under pressurized condition and usually is conducted under ordinary pressurized condition.

The reaction time defers depending on the conditions such as the solvent to be used and the reaction temperature, and it is usually 1 to 24 hours. The progress of the reaction can be confirmed by a conventional analytical means such as gas chromatography, high performance liquid chromatography, thin layer chromatography, NMR and IR.

After the completion of the reaction, for example, an organic layer containing an imidazo[1,2-b]pyridazine compound represented by the formula (2):

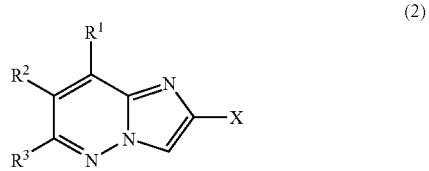

(hereinafter, simply referred to as the imidazo[1,2-b]pyridazine compound (2)) can be obtained by mixing the reaction mixture with water or an aqueous alkali solution followed by extracting, if necessary, by adding an organic solvent. The imidazo[1,2-b]pyridazine compound (2) can be isolated by concentrating the organic layer obtained. The imidazo[1,2-b]pyridazine compound (2) isolated may be further purified, for example, by a means such as recrystallization and column chromatography. Examples of the water-insoluble organic solvent include an aromatic hydrocarbon solvent such as toluene, xylene and mesitylene; an aliphatic hydrocarbon solvent such as decane; a halogenated aromatic hydrocarbon solvent such as monochlorobenzene; a halogenated aliphatic hydrocarbon solvent such as tetrachloroethane; an ester solvent such as ethyl acetate; an ether solvent such as diethyl ether and methyl tert-butyl ether; and a ketone solvent such as methyl ethyl ketone and methyl isobutyl ketone. The amount thereof to be used is not particularly limited.

Examples of the imidazo[1,2-b]pyridazine compound (2) thus obtained include 2-chloroimidazo[1,2-b]pyridazine, 2,6-dichloroimidazo[1,2-b]pyridazine, 6-methyl-2-chloroimidazo[1,2-b]pyridazine, 6-methoxy-2-chloroimidazo[1,2-b]pyridazine, 6-ethoxy-2-chloroimidazo[1,2-b]pyridazine, 6-trifluoromethyl-2-chloroimidazo[1,2-b]pyridazine, 4-methyl-2-chloroimidazo[1,2-b]pyridazine and 4,6-dimethyl-2-chloroimidazo[1,2-b]pyridazine.

EXAMPLES

The present invention will be further illustrated by Examples in detail below, but the present invention is not limited by these Examples. The analysis was conducted using the high performance liquid chromatography internal standard method.

Example 1

41.5 g of 3-imino-6-chloro-2,3-dihydropyridazine-2-acetic acid (content: 96.5% by weight) was mixed with 260 g of mixed xylene. To the mixture obtained, 98.1 g of phosphorus oxychloride was added at an inner temperature of 20 to 25° C. over 1 hour. To the mixture obtained, 32.4 g of triethylamine was added at an inner temperature of 10 to 40° C. over 2 hours followed by heating to an inner temperature of 120° C. over 3 hours. After reacting at the same temperature for 12 hours, the mixture was cooled to an inner temperature of 80° C. The reaction mixture obtained was added dropwise over 1 hour into 184.8 g of water adjusted at an inner temperature of 85° C. To this, 120 g of mixed xylene was added and 48% by weight aqueous sodium hydroxide solution was added to adjust pH of an aqueous layer to 4.5. An organic layer was obtained by separation procedure, and the organic layer was washed with 83 g of 1% by weight aqueous sodium hydroxide solution and then with 83 g of water. The organic layer after washing was concentrated to obtain 39.6 g of 2,6-dichloro[1,2-b]pyridazine (content: 97.0% by weight). The yield of 2,6-dichloro[1,2-b]pyridazine was 96%.

Example 2

1.88 g of 3-imino-6-chloro-2,3-dihydropyridazine-2-acetic acid (content: 99.5% by weight) was mixed with 3.64 g of 2-methyl-5-ethylpyridine. To the mixture obtained, 9.22 g of phosphorus oxychloride was added dropwise over 3 minutes at an inner temperature of 20 to 40° C. followed by heating to an inner temperature of 120° C. over 20 minutes. After reacting at the same temperature for 6 hours, the mixture was cooled to obtain the reaction mixture containing 2,6-dichloro[1,2-b]pyridazine The yield of 2,6-dichloro[1,2-b]pyridazine was 95%.

Example 3

According to the same manner as that described in Example 2, the reaction mixture containing 2,6-dichloroimidazo[1,2-b]pyridazine was obtained except that 4.70 g of dimethylaniline hydrochloride salt was used in place of 3.64 g of 2-methyl-5-ethylpyridine. The yield of 2,6-dichloro[1,2-b]pyridazine was 90%.

Example 4

1.88 g of 3-imino-6-chloro-2,3-dihydropyridazine-2-acetic acid (content: 99.5% by weight) was mixed with 7.52 g of monochlorobenzene and 0.79 g of pyridine. To the mixture obtained, 3.84 g of phosphorus oxychloride was added dropwise over 3 minutes at an inner temperature of 20 to 40° C. followed by heating to an inner temperature of 120° C. over 20 minutes. After reacting at the same temperature for 6 hours, the mixture was cooled to obtain the reaction mixture containing 2,6-dichloro[1,2-b]pyridazine. The yield of 2,6-dichloro[1,2-b]pyridazine was 99%.

Example 5

To the mixture prepared by mixing 10.0 g of 3-imino-6-chloro-2,3-dihydropyridazine-2-acetic acid (content: 98% by weight) with 62.7 g of xylene, 24.0 g of phosphorus oxychloride was added dropwise at an inner temperature of 10 to 30° C. followed by adding dropwise 15.8 g of triethylamine at an inner temperature of 10 to 50° C. The mixture obtained was heated to 120° C. After reacting at the same temperature for 21 hours, the mixture was cooled to obtain the reaction mixture containing 2,6-dichloro[1,2-b]pyridazine. The yield of 2,6-dichloro[1,2-b]pyridazine was 61%.

Example 6

To the mixture prepared by mixing 10.0 g of 3-imino-6-chloro-2,3-dihydropyridazine-2-acetic acid (content: 98% by weight) with 62.7 g of xylene, 12.0 g of phosphorus oxychloride was added dropwise at an inner temperature of 10 to 30° C. followed by adding dropwise 2.64 g of triethylamine at an inner temperature of 10 to 50° C. The mixture obtained was heated to 120° C. After reacting at the same temperature for 24 hours, the mixture was cooled to obtain the reaction mixture containing 2,6-dichloro[1,2-b]pyridazine The yield of 2,6-dichloro[1,2-b]pyridazine was 62%.

Example 7

To the mixture prepared by mixing 10.0 g of 3-imino-6-chloro-2,3-dihydropyridazine-2-acetic acid (content: 98% by weight) with 62.7 g of xylene, 24.0 g of phosphorus oxychloride was added dropwise at an inner temperature of 10 to 30° C. followed by adding dropwise 10.13 g of diisopropylethylamine at an inner temperature of 10 to 50° C. The mixture obtained was heated to 120° C. After reacting at the same temperature for 15 hours, the mixture was cooled to obtain the reaction mixture containing 2,6-dichloro[1,2-b]pyridazine. The yield of 2,6-dichloro[1,2-b]pyridazine was 73%.

Comparative Example 1

To 1.88 g of 3-imino-6-chloro-2,3-dihydropyridazine-2-acetic acid (content: 99.5% by weight), 9.22 g of phosphorus oxychloride was added dropwise over 3 minutes at an inner temperature of 20 to 40° C. The mixture obtained was heated to an inner temperature of 120° C. over 30 minutes. After reacting at the same temperature for 6 hours, the mixture was cooled to obtain the reaction mixture containing 2,6-dichloro[1,2-b]pyridazine The yield of 2,6-dichloro[1,2-b]pyridazine was 22%.

Comparative Example 2

1.88 g of 3-imino-6-chloro-2,3-dihydropyridazine-2-acetic acid (content: 99.5% by weight) was mixed with 7.29 g of 2-methyl-5-ethylpyridine. To the mixture obtained, 4.61 g of phosphorus oxychloride was added dropwise while keeping an inner temperature of 40° C. or less followed by heating to an inner temperature of 120° C. After reacting at the same temperature for 6 hours, the mixture was cooled to obtain the reaction mixture containing 2,6-dichloro[1,2-b]pyridazine. The yield of 2,6-dichloro[1,2-b]pyridazine was 0.4%.

INDUSTRIAL APPLICABILITY

According to the present invention, an imidazo[1,2-b]pyridazine compound, which is, useful as an intermediate of pharmaceuticals and pesticides, can be efficiently produced.

The invention claimed is:

1. A process for producing an imidazo[1,2-b]pyridazine compound represented by the formula (2):

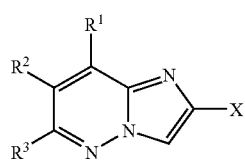

(2)

wherein $R^1$, $R^2$ and $R^3$ are the same or different and each represents a hydrogen atom, a halogen atom, an alkyl group which may be substituted with a halogen atom or atoms, an alkenyl group which may be substituted with a halogen atom or atoms, or an alkoxy group which may be substituted with a halogen atom or atoms, and X represents a halogen atom, wherein the process which comprises reacting a 2,3-dihydropyridazine compound represented by the formula (1):

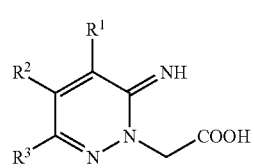

(1)

wherein $R^1$, $R^2$ and $R^3$ are the same meanings as defined above, with a phosphorus oxyhalide in the presence of an organic base which is in an amount of 0.5 mole or more relative to 1 mole of the 2,3-dihydropyridazine compound and 1 mole or less relative to 1 mole of the phosphorus oxyhalide.

2. The process for producing an imidazo[1,2-b]pyridazine compound according to claim 1, wherein the reaction temperature is 60 to 180° C.

3. The process for producing an imidazo[1,2-b]pyridazine compound according to claim 1, wherein the reaction temperature is 80 to 130° C.

4. The process for producing an imidazo[1,2-b]pyridazine compound according to claim 2, wherein the 2,3-dihydropyridazine compound is mixed with the phosphorus oxyhalide and the organic base at less than 60° C. and then the reaction is conducted at 60 to 180° C.

5. The process for producing an imidazo[1,2-b]pyridazine compound according to claim 3, wherein the 2,3-dihydropyridazine compound is mixed with the phosphorus oxyhalide and the organic base at less than 60° C. and then the reaction is conducted at 80 to 130° C.

\* \* \* \* \*